(12) United States Patent
Koyanagi et al.

(10) Patent No.: US 10,271,805 B2
(45) Date of Patent: Apr. 30, 2019

(54) ACCOMMODATION APPARATUS OF RADIATION IMAGING APPARATUS, ACCOMMODATION SYSTEM AND RADIATION IMAGING SYSTEM

(71) Applicant: CANON KABUSHIKI KAISHA, Tokyo (JP)

(72) Inventors: Takahiro Koyanagi, Kawasaki (JP); Hiroto Kondo, Yokohama (JP); Masaaki Kobayashi, Shimotsuke (JP); Youjirou Hiratsuka, Yokohama (JP); Takaaki Gonda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 247 days.

(21) Appl. No.: 15/283,565

(22) Filed: Oct. 3, 2016

(65) Prior Publication Data

US 2017/0112458 A1    Apr. 27, 2017

(30) Foreign Application Priority Data

Oct. 26, 2015   (JP) ................................. 2015-210011
Dec. 24, 2015   (JP) ................................. 2015-252018

(51) Int. Cl.
*A61B 6/00*    (2006.01)

(52) U.S. Cl.
CPC .............. *A61B 6/4283* (2013.01); *A61B 6/56* (2013.01)

(58) Field of Classification Search
CPC ...................................................... A61B 6/4283
See application file for complete search history.

(56) References Cited

U.S. PATENT DOCUMENTS

2013/0134930 A1*  5/2013  Konkle .................  H02J 7/0027
                                                320/108
2015/0180246 A1*  6/2015  Roth ....................  H02J 7/0027
                                                320/115

FOREIGN PATENT DOCUMENTS

JP          2009-237293 A    10/2009

* cited by examiner

*Primary Examiner* — Dani Fox
(74) *Attorney, Agent, or Firm* — Venable LLP

(57) ABSTRACT

An accommodation apparatus that accommodates a radiation imaging apparatus, the accommodation apparatus comprising: an accommodation unit including a bottom surface, a first wall surface adjacent to the bottom surface, and a second wall surface adjacent to the bottom surface and provided at a position facing the first wall surface, wherein the length in a horizontal direction of the first wall surface adjacent to the bottom surface and the length in the horizontal direction of the second wall surface adjacent to the bottom surface are different.

20 Claims, 12 Drawing Sheets

F I G. 11A
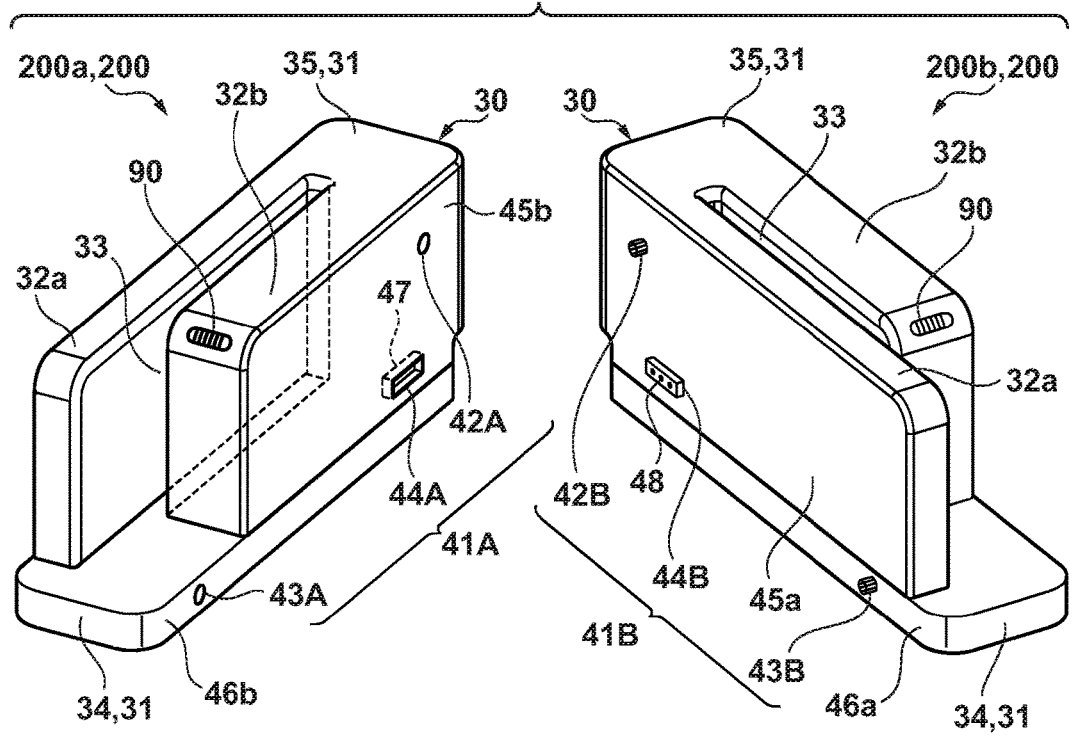
F I G. 11B
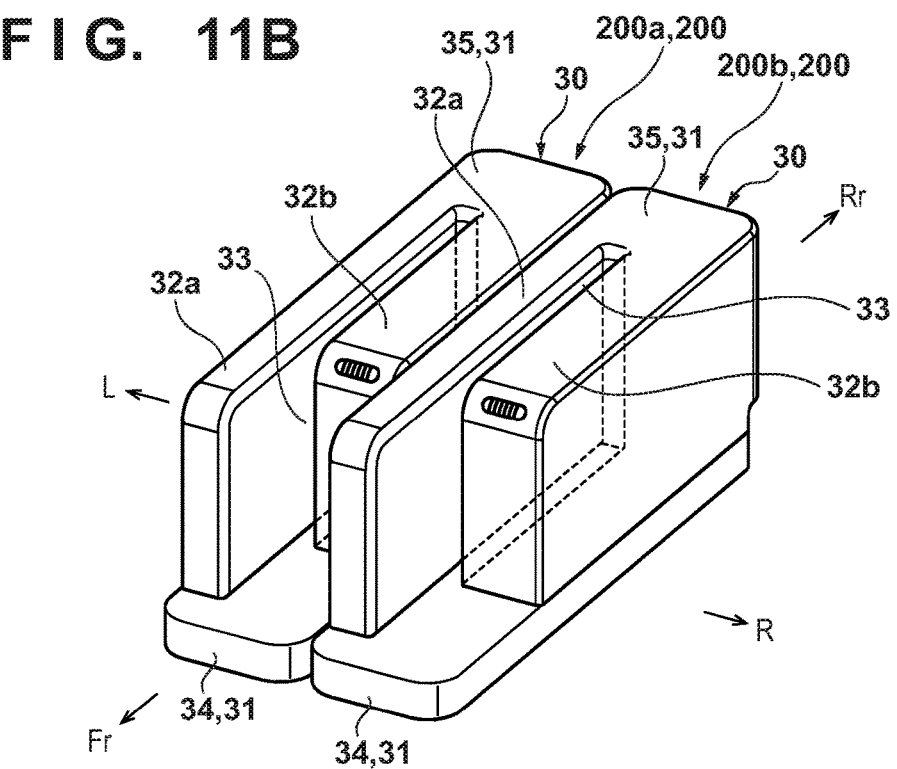

ACCOMMODATION APPARATUS OF RADIATION IMAGING APPARATUS, ACCOMMODATION SYSTEM AND RADIATION IMAGING SYSTEM

BACKGROUND OF THE INVENTION

Field of the Invention

The present invention relates to an accommodation apparatus of a radiation imaging apparatus, an accommodation system, and a radiation imaging system.

Description of the Related Art

Currently, portable digital radiation imaging apparatuses (cassettes) are being commercialized. Many of these are designed to match an external form of a film cassette of a standard size defined in JIS Z 4905 (ISO 4090). Also, in recent years, wireless cassettes that integrate a secondary battery and receive data from an external apparatus wirelessly have been developed. Also, accommodation apparatuses dedicated to such wireless cassettes have been developed.

In Japanese Patent Laid-Open No. 2009-237293, a cassette accommodation apparatus capable of handling various sizes of cassettes has been proposed. Also, in the accommodation apparatus of Japanese Patent Laid-Open No. 2009-237293, a configuration in which a cassette is inserted or extracted from a top surface of an insertion groove that is recessed in the shape of a valley has been proposed.

However, while the cassette accommodation apparatus recited in Japanese Patent Laid-Open No. 2009-237293 can accommodate a plurality of radiation imaging apparatuses, wasteful installation space is taken for users that only have one radiation imaging apparatus. Also, not enough consideration has been given to user operability at the time of insertion-extraction of the cassette. Accordingly, there is a problem in that it is difficult to make a radiation imaging apparatus insertion-extraction operation good while taking advantage of installation space effectively.

The present invention was conceived in view of the foregoing problem, and provides an accommodation apparatus for which a radiation imaging apparatus insertion-extraction operation is good and that takes advantage of installation space effectively.

SUMMARY OF THE INVENTION

According to one aspect of the present invention, there is provided an accommodation apparatus that accommodates a radiation imaging apparatus, the accommodation apparatus comprising: an accommodation unit including a bottom surface, a first wall surface adjacent to the bottom surface, and a second wall surface adjacent to the bottom surface and provided at a position facing the first wall surface, wherein the length in a horizontal direction of the first wall surface adjacent to the bottom surface and the length in the horizontal direction of the second wall surface adjacent to the bottom surface are different.

Further features of the present invention will become apparent from the following description of exemplary embodiments with reference to the attached drawings.

BRIEF DESCRIPTION OF THE DRAWINGS

FIGS. 11A-11B are views illustrating a cradle coupling structure according to an embodiment.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
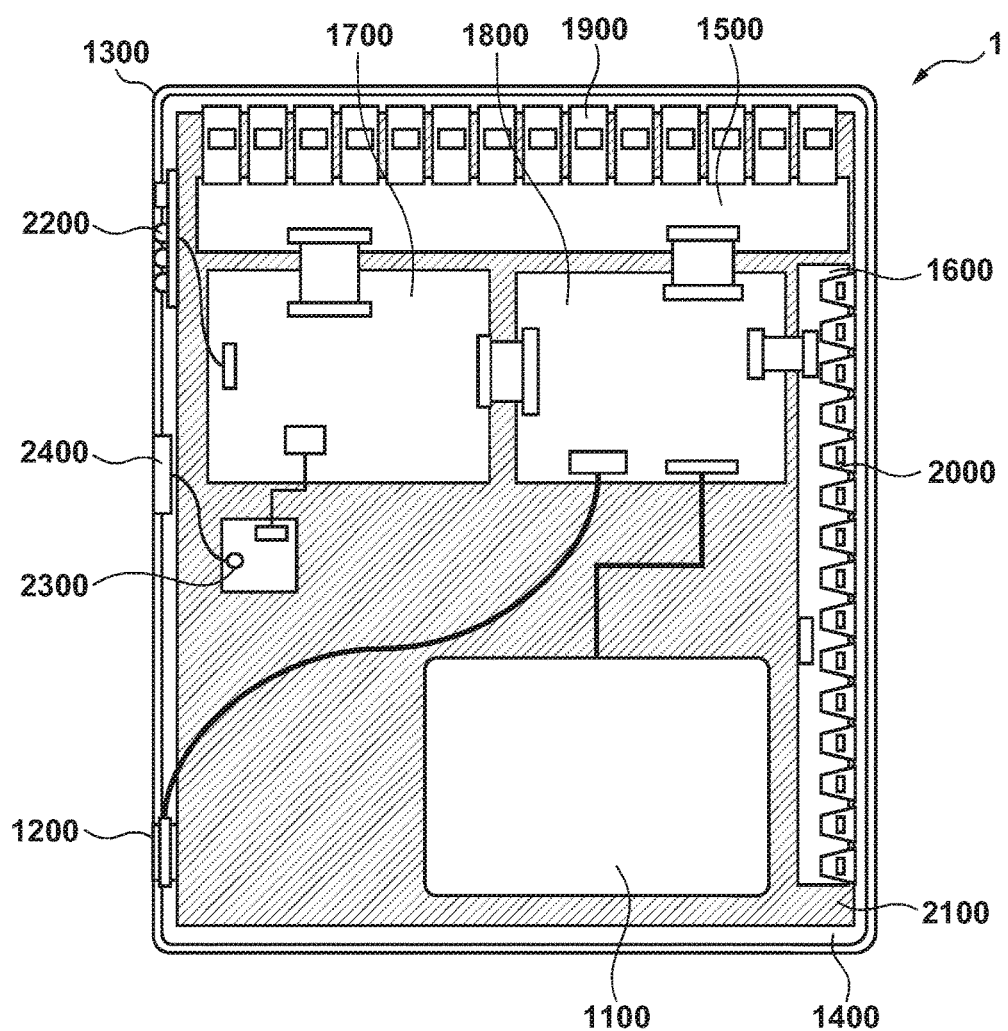
FIG. 1 is a planar cross sectional view of a radiation imaging apparatus (cassette) according to a first embodiment.
Figure 2:
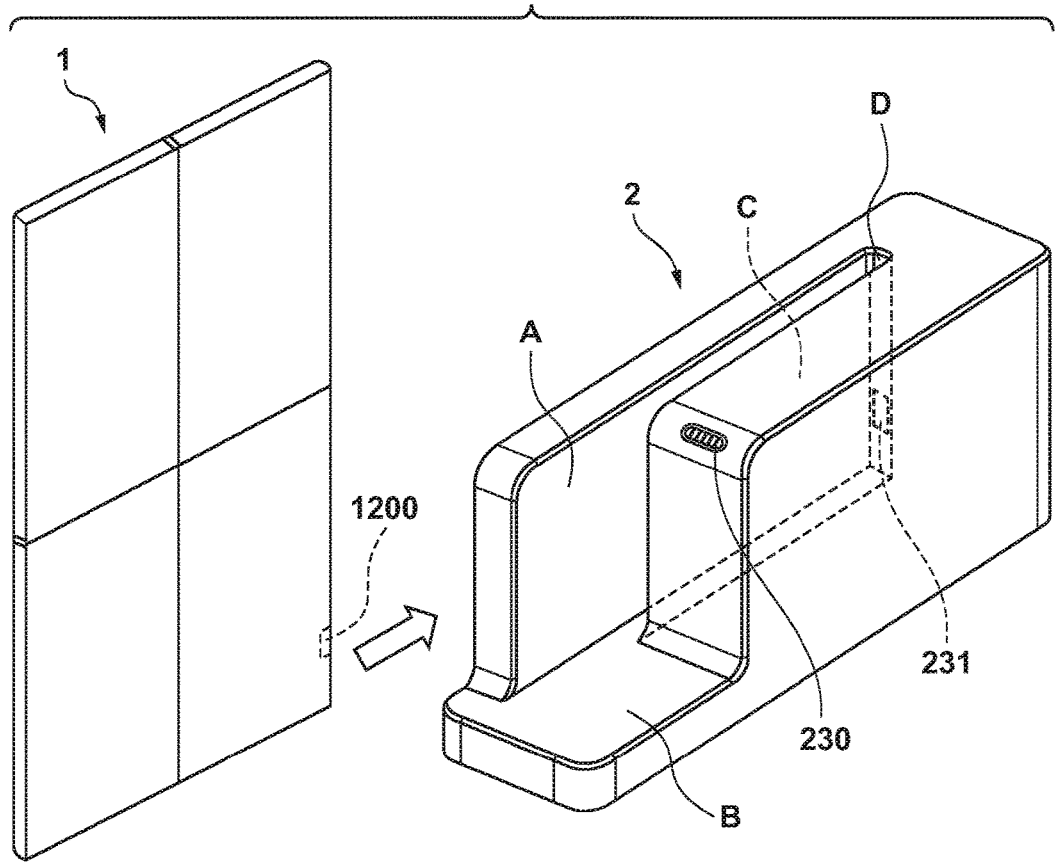
FIG. 2 is a perspective view of an accommodation apparatus (cradle) according to the first embodiment.
Figure 3:
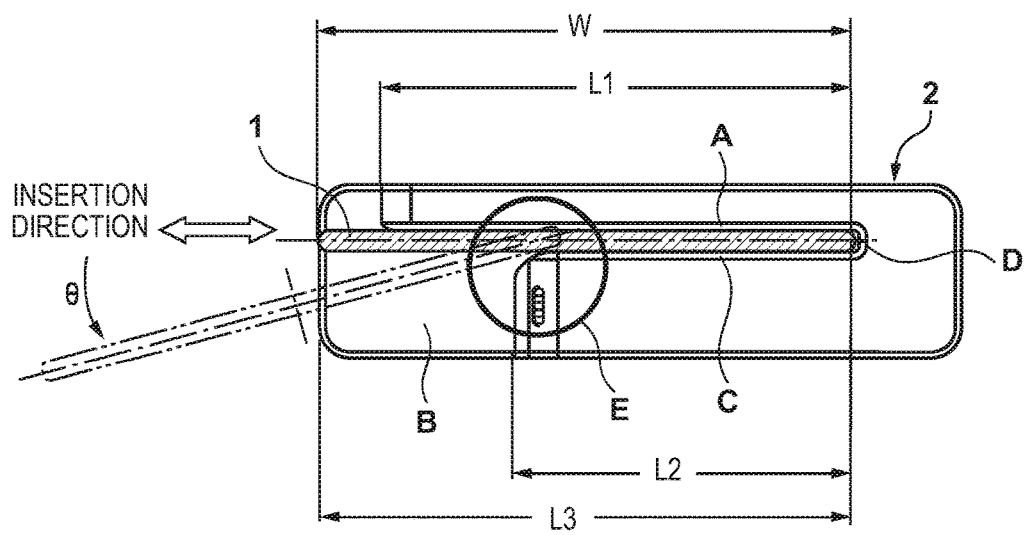
FIG. 3 is a plan view of the accommodation apparatus (cradle) according to the first embodiment.
Figure 4:
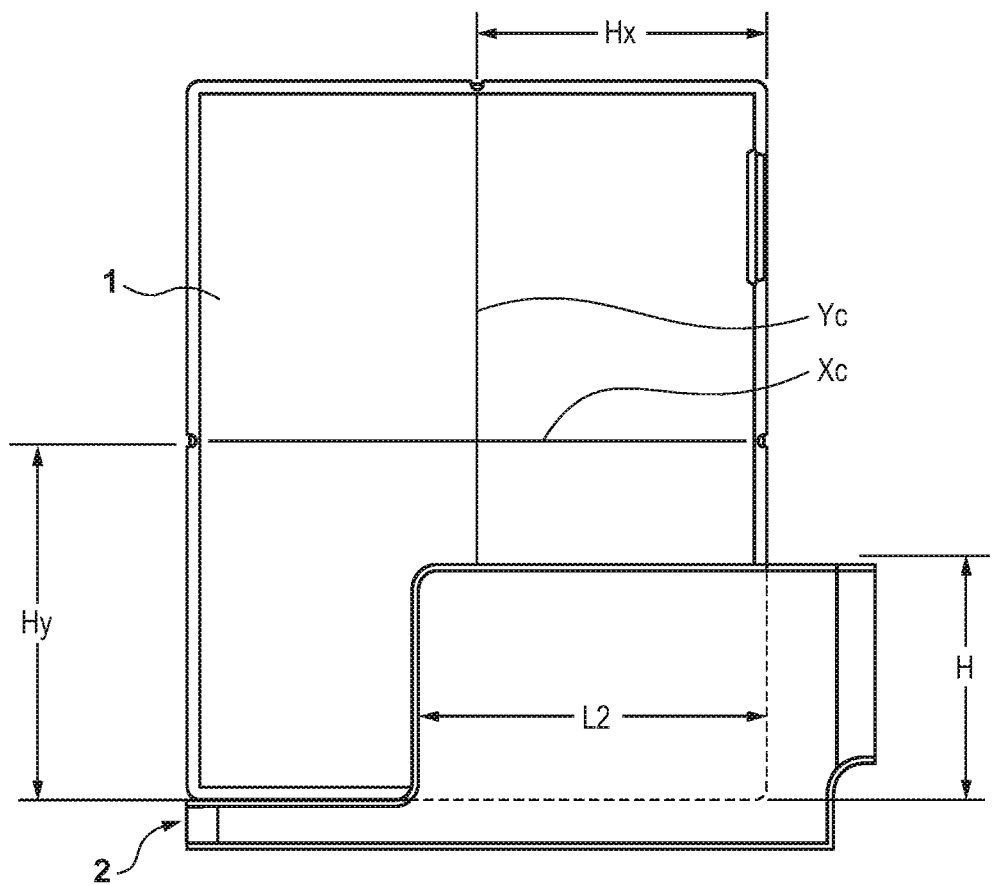
FIG. 4 is a side view of the accommodation apparatus (cradle) according to the first embodiment.

FIG. 1 is a planar cross sectional view illustrating a radiation imaging apparatus (cassette) from a surface face of a radiation incident surface in the present embodiment. FIG. 2 is a perspective view illustrating a cradle (accommodation apparatus) for charging in the present embodiment. FIG. 3 is a plan view in which a configuration in which the cassette is accommodated in the cradle for charging is seen from above in the present embodiment. FIG. 4 is a plan view in which a configuration in which the cassette is accommodated in the cradle for charging is seen from the side in the present embodiment.

A cassette 1 has an equivalent external size to a cassette standardized by JIS Z 4905. In a housing 1300 made up of a material for which a radiation incident surface side has a high radiation transmittance, a radiation detection panel 1400, and a support base 2100 are arranged in order from the radiation incident surface side.

The radiation detection panel 1400 is an image capturing panel on which a pixel device comprising a conversion element for converting a radiation dose into a charge amount, and a switch element for transferring an electric signal based on the charge amount are plurally arranged two-dimensionally on an insulating substrate (for example, a glass substrate). On the radiation detection panel 1400 a scintillator (not shown) is provided as a configuration for converting a radiation dose into a charge amount. The radiation detection panel 1400 is connected to a readout circuit 1500 for reading an electric signal from the pixel devices of the radiation detection panel 1400 via a flexible circuit board 1900. Also, via a flexible circuit board 2000, a driving circuit 1600 for supplying to a switch element a drive signal having a voltage for turning on the switch element is connected.

The radiation detection panel 1400 is held via a radiation shielding member (not shown) comprising a material including a heavy metal of any of, for example, Pb, Ba, Ta, Mo, and W, and a material for shielding radiation such as a stainless steel on a first surface which is the radiation incident surface side of the support base 2100, or a second surface on the opposite side to the first surface. Also, a wireless module unit 2300 that functions as a wireless reception unit and a wireless transmission unit for wireless transmission of image signals to the readout circuit 1500, the driving circuit 1600, various control circuits 1700 and 1800 for controlling electric signal control, direct-current voltage conversion or the like, a secondary battery 1100 for the supplying power for driving, and external apparatuses is arranged on the second surface on the opposite side of the first surface of the support base 2100. Also, on a surface (for example, a side surface) other than the radiation incident surface of the housing 1300, an external connection terminal 1200 for performing data communication or power supply from an external apparatus, an antenna unit 2400, and a user IF unit 2200 that implements a power ON/OFF switch or a status display unit are arranged.

As illustrated in FIG. 2, a cradle 2 is an accommodation apparatus that accommodates the cassette 1, and it comprises an accommodation unit having a bottom surface portion B, a first wall surface A adjacent to the bottom surface portion B, and a second wall surface C adjacent to the bottom surface portion B and provided at a position facing the first wall surface A. Also, the accommodation unit further includes a third wall surface D adjacent to the bottom surface portion B, the first wall surface A, and the second wall surface C.

Configuration is such that a power supply connector 231 provided on the cradle 2 and the external connection terminal 1200 of the cassette 1 connect by accommodating the cassette 1 in the slot portion (accommodation unit) of the cradle 2 illustrated in FIG. 2, and thereby charging of the secondary battery 1100 of the cassette 1 is enabled. In such a case, the power supply connector 231 functions as a power supply unit that performs a power supply to charge the cassette 1. Also, an LED display unit 230 is provided in the cradle 2, and can display a charge status of the secondary battery 1100. The arrangement position of the LED display unit 230 is not limited to the example of FIG. 2, and can be provided at any position on the cradle 2. Also, in the case of a configuration in which the cradle 2 is capable of a power supply in a non-contacting manner for the cassette 1, it comprises a power supply unit for handling this. In such a case, the cradle 2 can be configured with a power supply coil and a power supply antenna in place of the power supply connector 231 as a power supply unit having the power supply function.

Also, as illustrated in FIG. 3, lengths L1 (the length in a horizontal direction of the first wall surface A) and L2 (the length in a horizontal direction of the second wall surface C) of the walls of the cradle 2 that hold the cassette 1 are configured to be shorter than a length L3 of the bottom surface portion B. If the length L1 and the length L2 are different, and the user operates from a vertical position in insertion-extraction directions, when pulling out, it is possible to pull out by operating using one hand until L2, and then changing the direction of the cassette 1 to a direction of the angle θ with the bottom surface portion B as support and holding with both hands, and so the operation from pulling out to holding can be performed smoothly. The operation for insertion becomes easy when inserting between the walls L1 and L2 by placement against the bottom surface portion B and the wall L1. Also, on the second wall surface C, the end portion of the edge on the side at which the cassette 1 is inserted or extracted has an inclined portion E. By comprising the inclined portion E, it is possible to make the operation of changing the direction of the cassette 1 to the direction of the angle θ in a state in which it is caused to contact the second wall surface C smoother.

Using FIG. 4, explanation is given for a relation between a length of a wall of the cradle 2, and a length W of the cassette 1. As illustrated in FIG. 4, configuration is such that the length L1 of a wall of the cradle 2 and a length W of the cassette 1 satisfy the relation W>L1, and/or the height H of the wall of the cradle 2 and the height Hy to a center line Xc of the cassette 1 satisfy the relation Hy>H. That is, the length H in a vertical direction of the first wall surface A and the second wall surface B is configured to be shorter than the length Hy which is half the length in the vertical direction in a case where the cassette 1 is accommodated, and/or the length L2 in the horizontal direction of the second wall surface C is configured to be shorter than a length Hx which is half the length in a horizontal direction in a case where the cassette 1 is accommodated. It is sufficient that at least one of these relations holds.

Considering the stability in the case where the cassette 1 is accommodated, it is advantageous that the length L2 of the shorter wall be a length greater than or equal to the length Hx which is half of the cassette 1 (L2>Hx). By this, even if the user performs an operation holding close to the central portion of the edge of the cassette 1, it is possible to prevent the hand of the user and the cradle 2 from contacting upon insertion-extraction, and so it is possible to improve operability. Also, even if a plurality of the cradle 2 which accommodates the cassette 1 are installed adjacent to each other, the influence on operability is small since the cassette 1 can move in the range of the angle θ. Accordingly, it is possible to effectively take advantage of the installation space.

As explained above, by virtue of the configuration of the first embodiment, even if there are a plurality of radiation imaging apparatuses (cassettes), it is possible to effectively take advantage of the installation space, and it is possible to provide an accommodation apparatus (cradle) for which an operation to insert-extract a radiation imaging apparatus is good.

Second Embodiment

In the first embodiment, explanation is given of a cradle for charging by which operability is improved by making the lengths of the two walls that hold the cassette different. In the second embodiment, specific explanation is given with reference to FIG. 5 for cassette insertion-extraction operability in a case where a plurality of cradles are installed adjacent to each other.

Figure 5:
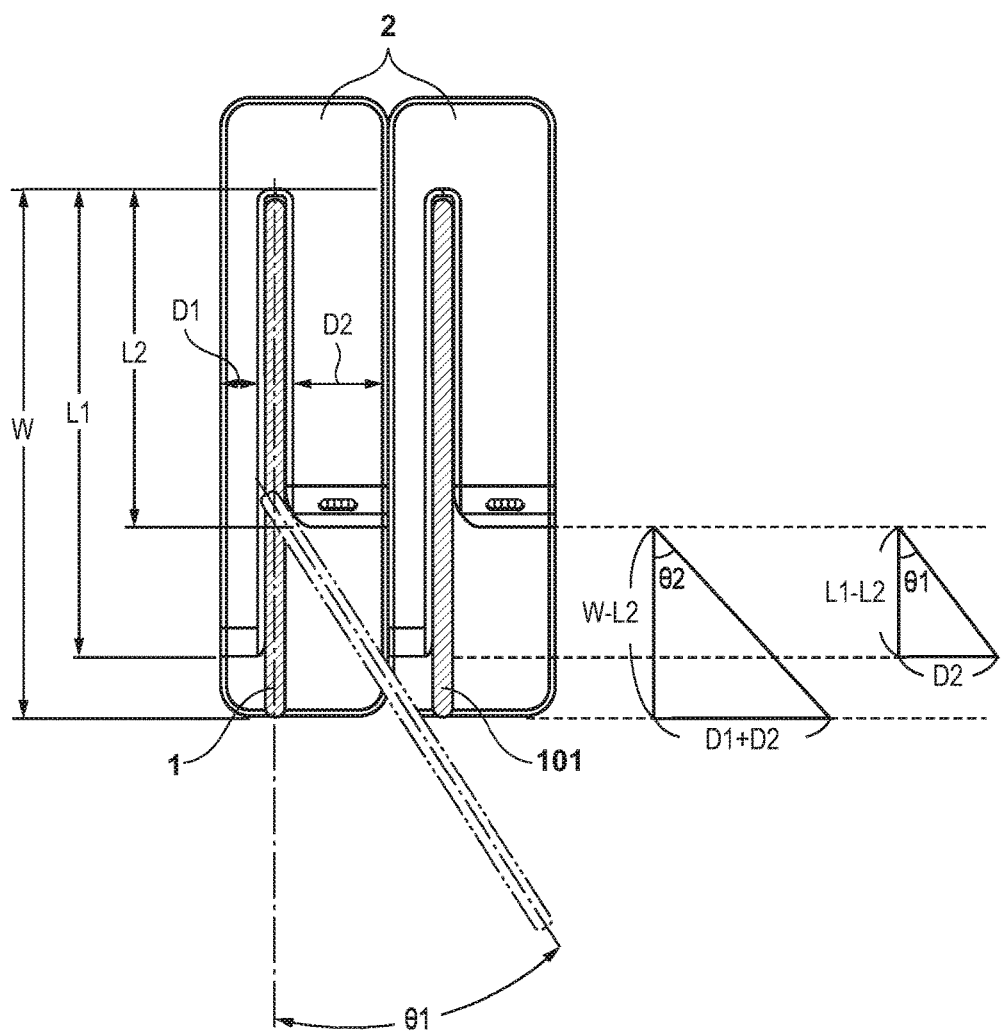
FIG. 5 is a plan view of the accommodation apparatus (cradle) according to a second embodiment.

FIG. 5 is a plan view for when a configuration in which two devices are installed adjacent to each other, and in which the cassette 1 is accommodated in the cradle 2 for charging is viewed from above in the present embodiment.

The width (thickness) of the wall of the length of L1 of the cradle 2 that holds the cassette 1 is assumed to be D1, and the width (thickness) of the wall of the length of L2 is assumed to be D2. That is, the thickness of a first wall surface portion comprising the first wall surface A is D1, and the thickness of a second wall surface portion comprising the second wall surface C is D2. Also, the angle at the time of insertion-extraction of the cassette 1 is made to be θ1.

Configuration is such that if L1>L2, D1<D2. Meanwhile, configuration is such that if L1<L2, D1>D2. If L1>L2, tan θ1=D2/(L1−L2), and tan θ2=(D1+D2)/(W−L2). The dimensional shape relation of tan θ1=D2/(L1−L2)<tan θ2=(D1+D2)/(W−L2), that is the relation θ1<θ2.

Also, dimensions such that the relation θ1>25 degrees holds are advantageous, and it becomes possible to insert-extract without contacting a cassette 101 accommodated in a cradle adjacently installed in a state of inclination of the angle θ1 upon attachment/detachment of the cassette 1.

As explained above, by virtue of the configuration of the second embodiment, even if there are a plurality of radiation imaging apparatuses (cassettes), it is possible to effectively take advantage of the installation space, and it is possible to provide an accommodation apparatus (cradle) for which an operation to insert-extract a radiation imaging apparatus is good.

Third Embodiment

In the first and second embodiments, explanation is given of a cradle for charging by which operability is improved by making the lengths of the two walls that hold the cassette different. However, this configuration did not consider operability in a case where the positional relationship does not correspond to the desired operation position of the user in relation to the cradle accommodation direction in regards to the installation environment or the user's dominant arm. In the third embodiment, explanation is given of a cradle for which the left-right length relation of the portions that hold the cassette can be changed.

Figure 6A:
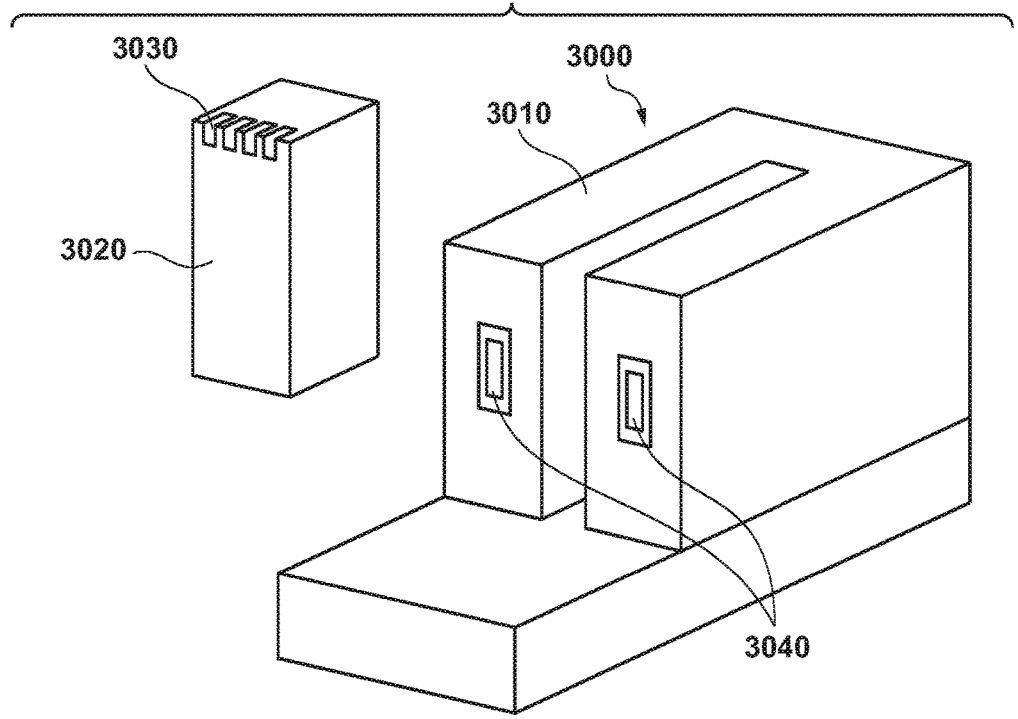
FIGS. 6A-6B are perspective views of an accommodation apparatus (cradle) according to a third embodiment.
Figure 6B:
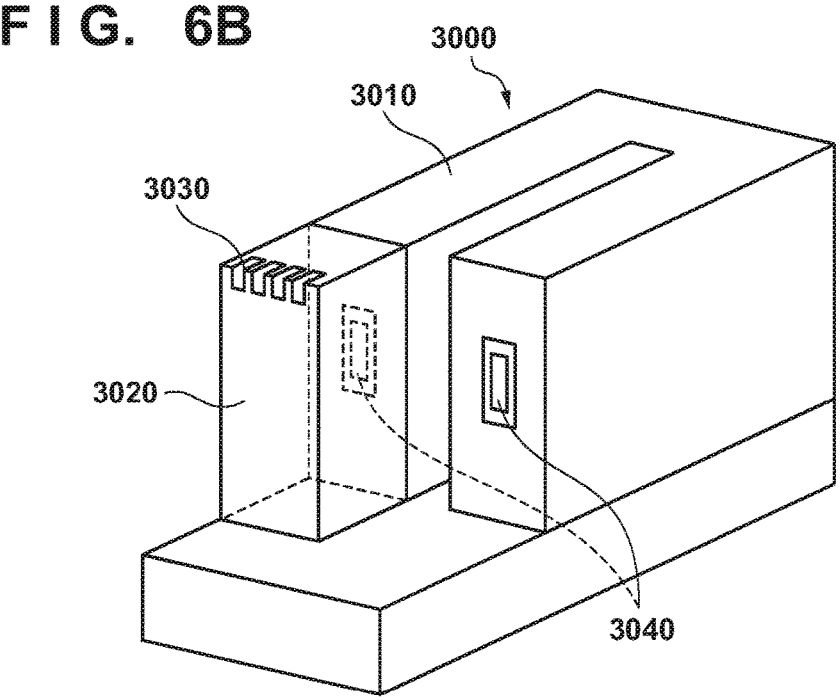

FIG. 6A and FIG. 6B are perspective views illustrating a cradle 3000 for charging in a state in which the cassette 1 is accommodated in the present embodiment. The cradle 3000 comprises a first housing unit 3010 for which the walls of the portions that hold the cassette are of the same length, and a second housing unit 3020 that comprises an LED display unit 3030, and is configured such that it can be attached/detached to/from the first housing unit 3010. Connector units 3040 by which it is possible to electrically connect the second housing unit 3020 are arranged at two locations on left and right wall surfaces of the first housing unit 3010, and it is possible for the user to freely select which to align the connection position of the second housing unit 3020 with.

As explained above, by virtue of the configuration of the third embodiment, it is possible to provide an accommodation apparatus (cradle) for which the user can change the length of the left and right walls of the portions that hold the cassette by freely aligning. By this, it is possible to provide an accommodation apparatus (cradle) that effectively takes advantage of installation space even if there is a plurality of radiation imaging apparatuses (cassettes) without being affected by the installation environment or the user's dominant arm, and for which the radiation imaging apparatus insertion-extraction operation is good.

By virtue of the present invention, it is possible to effectively take advantage of the installation space and to provide an accommodation apparatus for which the radiation imaging apparatus insertion-extraction operation is good.

Fourth Embodiment

A radiation imaging system of the present embodiment comprises a radiation imaging apparatus and an accommodation apparatus.

Firstly, explanation is given for the radiation imaging apparatus (hereinafter referred to as a cassette 100).

Figure 7A:
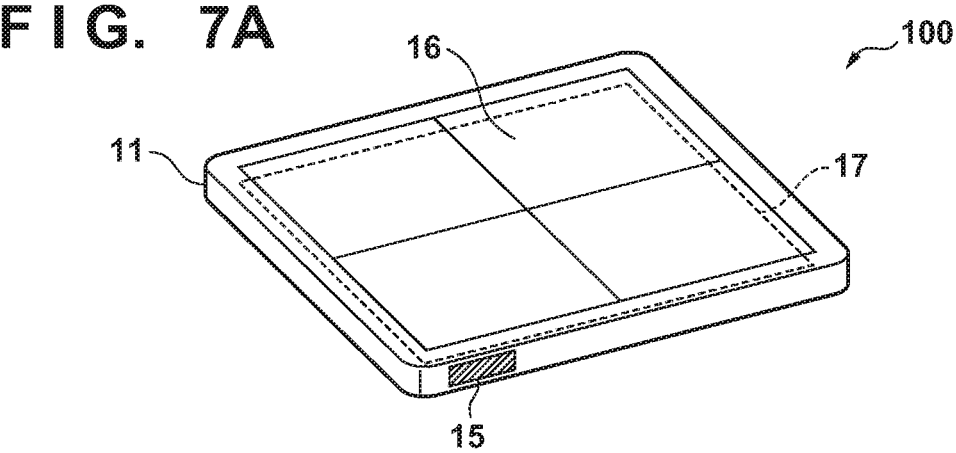
FIGS. 7A-7B are perspective views illustrating an outer appearance of the cassette according to an embodiment.
Figure 7B:
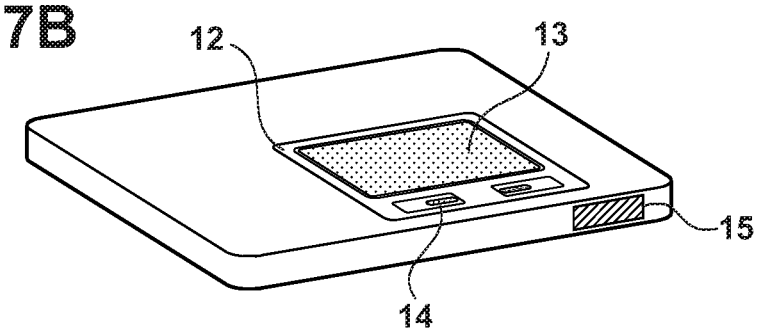
Figure 8:
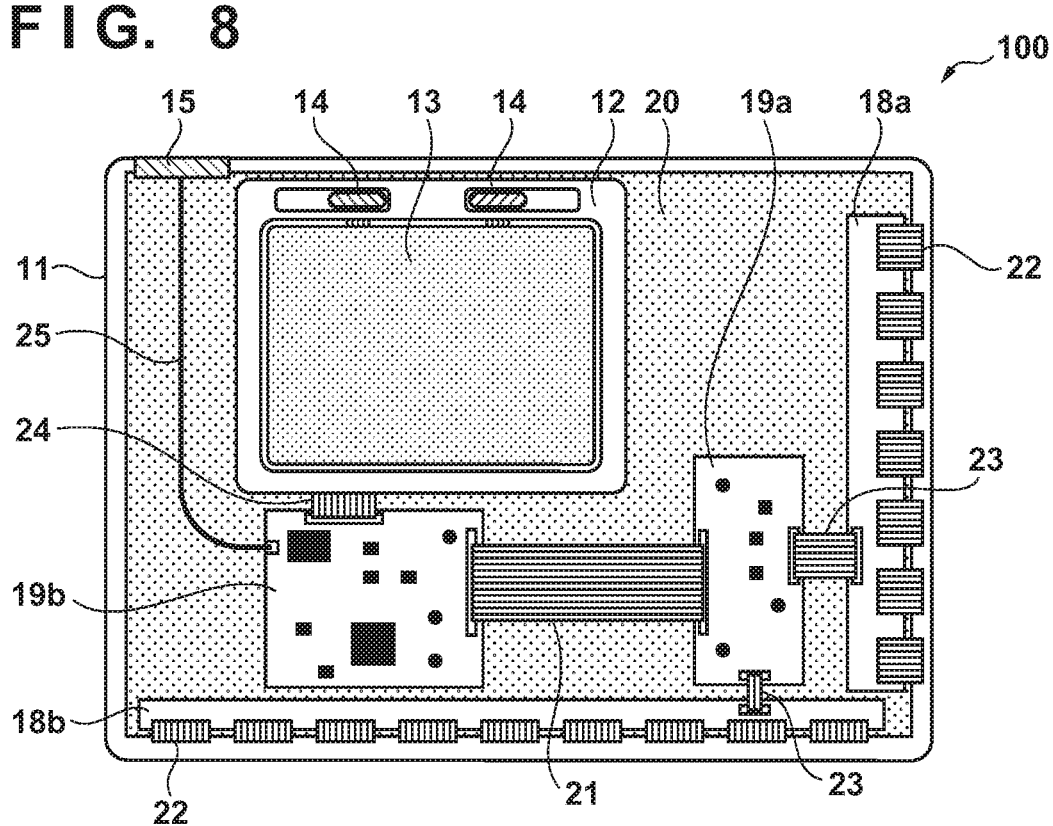
FIG. 8 is a view illustrating a configuration of an interior of the cassette according to an embodiment.

FIGS. 7A-7B are perspective views illustrating an outer appearance of the cassette 100; FIG. 7A illustrates a side of the incident surface and FIG. 7B illustrates a back surface side (the surface on the opposite side of the incident surface). FIG. 8 is a view illustrating an interior configuration of the cassette 100.

The cassette 100 comprises a housing 11 and a radiation transmissive plate 16 as exterior covering.

The housing 11 has a large opening portion on the incident surface side of the radiation. For the housing 11, lightweight, high-rigidity material is used. Specifically, it is possible to apply an aluminum alloy, a magnesium alloy, or a CFRP (carbon fiber-reinforced plastic) to the housing 11. By making the housing 11 an exterior covering of the cassette 100, it is possible to protect each component in the cassette 100.

Also, for the housing 11, a battery holder 12 is provided on the back surface side, and a battery 13 is held such that attachment/detachment is possible. When the battery 13 is mounted to the battery holder 12, the cassette 100 operates by power of the battery 13 being supplied to each unit of the cassette 100. The battery 13 can be separated from the battery holder 12 by a battery lock 14 being operated to unlock it. The battery 13 is a secondary battery, and for example a lithium ion battery, a capacitor, or the like, can be applied.

Also, for the housing 11, a terminal 15 is provided on one side surface (a surface orthogonal to the incident surface and the back surface). The terminal 15 is used in cases where power is received from the later described cradle, or communication with an external apparatus or the system is performed.

The radiation transmissive plate 16 is arranged at an opening portion of the housing 11. For the radiation transmissive plate 16, material that transmits radiation easily is used. For the radiation transmissive plate 16, for example CFRP or the like is used. Note that if the housing 11 is CFRP, it can be configured in a single body with the radiation transmissive plate 16 without providing an opening portion in the housing 11.

Also, the cassette 100 internally comprises a sensor 17 (refer to FIG. 7A) as a radiation detector, circuit boards 18a and 18b, electronic substrates 19a and 19b, a holding board 20, and the like.

A flat panel detector (FPD) can be applied to the sensor 17. The flat panel detector comprises a substrate, photoelectric conversion elements arranged two-dimensionally on the surface of the substrate, and a layer of scintillator (a layer of fluorescent body) provided so that it is stacked on the photoelectric conversion elements. In the flat panel detector, the layer of scintillator emits light when radiation transmitted through an object is incident, and the photoelectric conversion elements detect the emission and convert it into an electric signal. GOS (Gd2O2S) or CsI can be applied to the fluorescent body.

The circuit boards 18a and 18b read out the electric signal converted by the sensor 17. The circuit boards 18a and 18b and the sensor 17 are connected via a flexible cable 22.

Electronic substrates 19a and 19b generate image data as a radiation image from an electric signal read by the circuit boards 18a and 18b. The electronic substrate 19a and the electronic substrate 19b are connected via a flexible cable 21. Also, the electronic substrate 19a is connected via the circuit boards 18a and 18b and a flexible cable 23. Also, the electronic substrate 19b is connected via the battery 13 and a flexible cable 24.

The holding board 20 holds the sensor 17, the circuit boards 18a and 18b, and the electronic substrates 19a and 19b. Specifically, the holding board 20 holds the sensor 17 on the incident surface side, and holds the circuit boards 18a and 18b and the electronic substrates 19a and 19b on the opposite side to the incident surface side.

Image data generated by the electronic substrates 19a and 19b is transmitted to the exterior via the terminal 15, and displayed by an external display system. Here, the electronic substrate 19b is connected to the terminal 15 via a cable 25. Note that transmission of image data may also be wireless and limitation is not made to the wired case. In the case of wireless, it is possible to mainly use 2.4 GHz and 5 GHz bands. By causing the image data transmitted in this way to be displayed by a PC, a tablet or the like, it is possible for the user to confirm image data.

Next, explanation is given for an accommodation apparatus of the cassette 100 (hereinafter referred to as a cradle 200).

Figure 9:
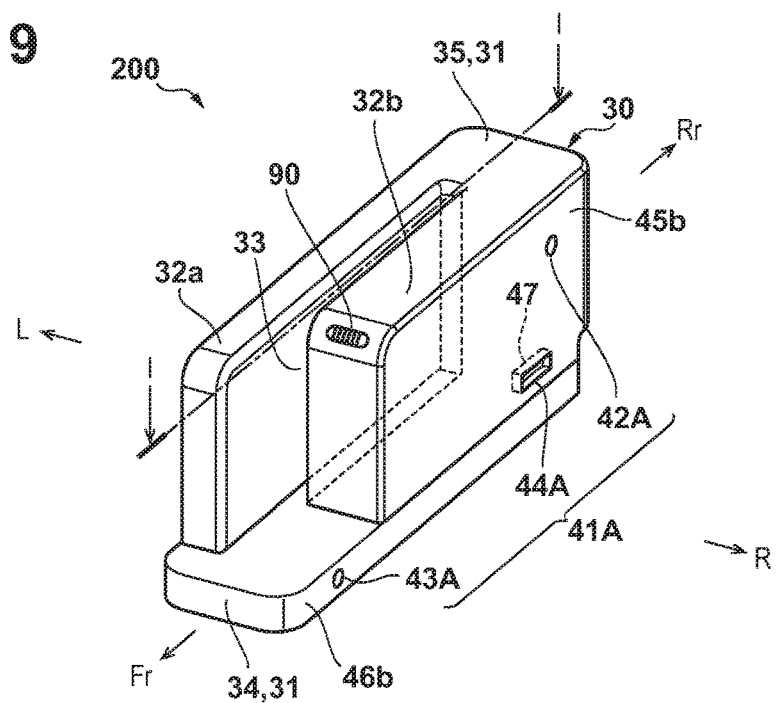
FIG. 9 is a perspective view illustrating a configuration of the cradle of a fourth embodiment.
Figure 10:
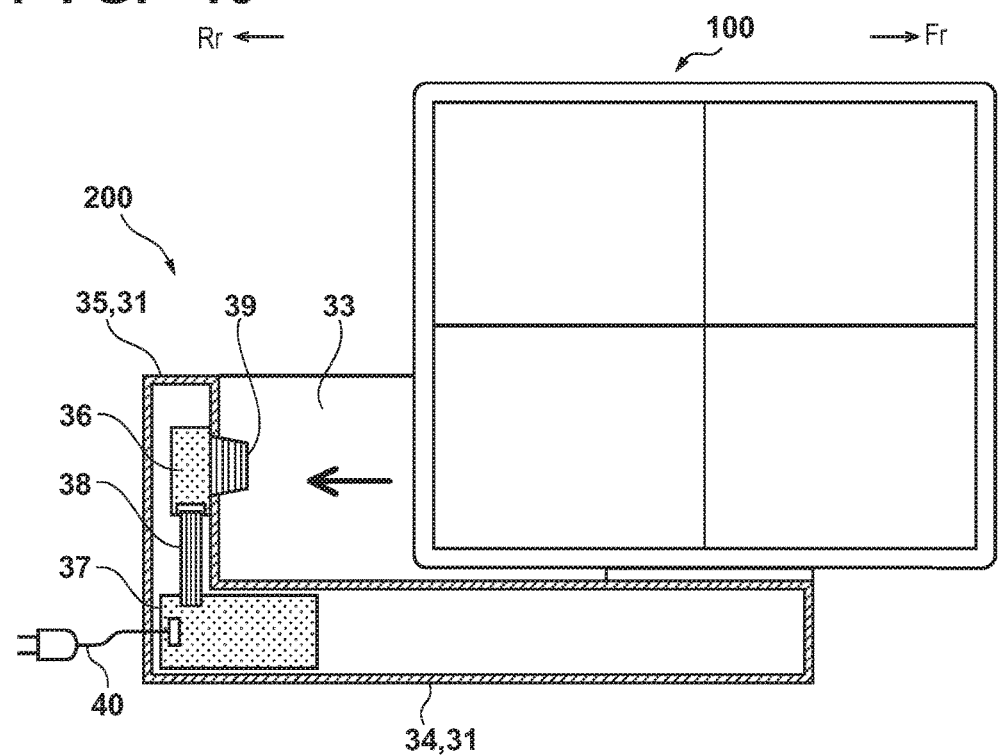
FIG. 10 is a cross-sectional view illustrating a configuration of the cradle according to an embodiment.

FIG. 9 is a perspective view illustrating a configuration of the cradle 200. FIG. 10 is a cross-sectional view from a perspective of a lateral direction (left side) that cuts FIG. 9 in an arrow symbol direction along an I-I line. Note that below in the respective figures to simplify the explanation the right side of the cradle is shown as R, the left side L, the front side Fr, and the rear side Rr as necessary.

The cradle 200 can accommodate the cassette 100, and charges the battery 13 of the accommodated cassette 100. The cradle 200 of the present embodiment is of a type where the number of slots for accommodating the cassette 100 is one. Explanation is given of a specific configuration below.

The cradle 200 has a housing unit 30 that accommodates the cassette 100. The housing unit 30 is substantially a rectangular parallelepiped that is longer front and back than left and right.

For the housing unit 30 of the present embodiment, a main body unit 31 and the side wall portions 32a and 32b are configured as a single body. A side wall portion 32a and a side wall portion 32b are arranged to face each other via a gap. A space surrounded by the main body unit 31 and the side wall portions 32a and 32b is an accommodation unit 33 which is a slot for accommodating the cassette 100.

The main body unit 31 comprises a bottom portion 34 and a support portion 35. The bottom portion 34 contacts an installation surface of the cradle 200, and supports one side surface of the cassette 100 accommodated in the accommodation unit 33. The support portion 35 is arranged to stand in a single body from the rear side of the bottom portion 34, and supports another one side surface of the cassette 100 accommodated in the accommodation unit 33. Note that the interior of the bottom portion 34 and the support portion 35 is hollow as illustrated in FIG. 10.

Also, electronic substrates 36 and 37 are arranged in the interior of the main body unit 31. The electronic substrate 36 and the electronic substrate 37 are connected via a cable 38.

Here, a power supply unit 39 is connected to the electronic substrate 36. The power supply unit 39 is provided so as to project from the support portion 35 towards the accommodation unit 33, and to be exposed in the accommodation unit 33. That is, the power supply unit 39 is positioned on the deepest side of the accommodation unit 33. By accommodating the cassette 100 in the accommodation unit 33, the terminal 15 of the cassette 100 and the power supply unit 39 are connected.

A power supply cable 40 is connected to the electronic substrate 37. The power supply cable 40 extends from the main body unit 31 to the exterior. Accordingly, by connecting the power supply cable 40 to an outlet, power is supplied to the electronic substrates 36 and 37, and the battery 13 is charged by power supply to the cassette 100 accommodated in the accommodation unit 33 via the power supply unit 39.

The side wall portion 32a is positioned on the left side in a left-right direction of a housing unit 10, and supports one side of the incident surface side and a back surface side of the cassette 100 accommodated in the accommodation unit 33. The side wall portion 32b is positioned on the right side in a left-right direction of the housing unit 10, and supports the other of the incident surface side and a back surface side of the cassette 100 accommodated in the accommodation unit 33. Note that in the present embodiment, the front-back dimension of the side wall portion 32a is longer than the front-back dimension of the side wall portion 32b, and left-right dimension of the side wall portion 32a is shorter than the left-right dimension of the side wall portion 32b.

Also, the side wall portion 32b comprises a display unit 90 on the front side and the top side. The display unit 90 displays the current amount of charge, energization state (whether it is energized, whether charging is complete), charging errors or the like for the battery 13 of the cassette 100 accommodated in the accommodation unit 33. Accordingly, it is possible for a user to confirm the state of the battery 13 via the display unit 90.

Next, explanation is given for a configuration for installing a plurality of the cradle 200 in a space economical manner. In the present embodiment, because space-saving when installing a plurality of the cradle 200 is attempted, the cradles 200 are coupled to each other via later described coupling portions.

FIGS. 11A-11B are perspective views illustrating the coupling structures of the cradle 200. FIG. 11A illustrates a state in which two of the cradles 200 are separated, and FIG. 11B illustrates an accommodation system in which two of the cradles 200 are coupled. Here, a cradle 200a is explained as the left side and a cradle 200b as the right side.

The housing unit 30 of the cradle 200a comprises coupling portions 41A, and the housing unit 30 of the cradle 200b comprises coupling portions 41B coupled to the coupling portions 41A.

Firstly, the coupling portions 41A are explained.

The coupling portions 41A comprise engaging portions 42A and 43A and a connector unit 44A. The engaging portion 42A and the connector unit 44A are provided on the side surface 45b on the opposite side of the accommodation unit 33 side in the side wall portion 32b, and the engaging portion 43A is provided on the side surface 46b on the same side as the side surface 45b in the bottom portion 34. Here, the engaging portion 42A is positioned on the top side and the rear side, and the engaging portion 43A is positioned on the bottom side and the front side. Meanwhile, the top-bottom position of the connector unit 44A is between the engaging portion 42A and the engaging portion 43A, and the front-back position is between the engaging portion 42A and the engaging portion 43A.

In the present embodiment, the engaging portion 42A and the engaging portion 43A are of a circular shape formed as cavities on the side surface 45b and the side surface 46b respectively, and they function as fitting holes.

The connector unit 44A is of a rectangular hole form formed as a cavity in the side surface 45b, and an electrode unit 47 is arranged internally. The electrode unit 47 is connected to the electronic substrate 37 in the housing unit 30.

Next, the coupling portions 41B are explained.

The coupling portions 41B comprise engaging portions 42B and 43B and a connector unit 44B. The engaging portion 42B and the connector unit 44B are provided on the side surface 45a on the opposite side of the accommodation unit 33 side in the side wall portion 32a, and the engaging portion 43B is provided on the side surface 46a on the same side as the side surface 45a in the bottom portion 34. Here, the engaging portion 42B is positioned on the top side and the rear side, and the engaging portion 43B is positioned on the bottom side and the front side. Meanwhile, the top-bottom position of the connector unit 44B is between the engaging portion 42B and the engaging portion 43B, and the front-back position is between the engaging portion 42B and the engaging portion 43B.

In the present embodiment, the engaging portion 42B and the engaging portion 43B are of a circular shape respectively projecting in a convex shape from the side surface 45a and the side surface 46a respectively, and they function as fitting bosses.

The connector unit 44B is of a rectangular projection that projects in a convex shape from the side surface 45a, and an electrode unit 48 is arranged on its proximal end. The electrode unit 48 is connected to the electronic substrate 37 in the housing unit 30.

Next, explanation is given of a case in which the cradles 200 are coupled to each other.

Firstly, the user causes the side wall portion 32b of the cradle 200a and the side wall portion 32a of the cradle 200b to face each other. At this time, the engaging portion 42A and the engaging portion 42B, the engaging portion 43A and the engaging portion 43B, and the connector unit 44A and the connector unit 44B respectively face each other. Next, the user pushes the cradle 200a and the cradle 200b in directions to cause them to approach each other. Then, the engaging portion 42B is inserted and fits into the engaging portion 42A, and the engaging portion 43B is inserted and fits into the engaging portion 43A. Also, the connector unit 44B is inserted into the connector unit 44A, and the electrode unit 47 and the electrode unit 48 contact and are connected electrically. Accordingly, as illustrated in FIG. 11B, coupling is achieved in a state in which the side wall portion 32b of the cradle 200a and the side wall portion 32a of the cradle 200b contact.

In this way, by the cradle 200a comprising the coupling portions 41A, and the cradle 200b comprising the coupling portions 41B which are coupled with the coupling portions 41A, it is possible to install in a state in which the cradle 200a and the cradle 200b are coupled. Accordingly, because it is possible to put the cradles 200a and 200b into a state in which they are approach each other, it is possible to achieve economization of installation space even in a case of installing a plurality of the cradle 200. Because the engaging portions 42A and 43A and the engaging portions 42B and 43B are fit together here, it is possible to prevent the coupling between the cradle 200a and the cradle 200b being easily unlocked.

Meanwhile, if only one of the cassette 100 is needed, it is possible for the user to unlock the coupling by pulling the cradle 200a and the cradle 200b apart. Accordingly, it is possible to install only one cradle 200 corresponding to one cassette 100, and it is possible to achieve space-saving of installation space.

Also, by the electrode unit 47 of the cradle 200a and the electrode unit 48 of the cradle 200b being connected electrically, power transmission/reception and communication between the cradle 200a and the cradle 200b is possible via the electrode units 47 and 48. In such a case, the electronic substrate 37 of either the cradle 200a or the cradle 200b may control transmission/reception of power. For example, a case where the cradle 200a is assumed to be a higher level cradle, and the cradle 200b is assumed to be a lower level cradle, and the cradle 200b does not comprise the power supply cable 40. In such a case, power to the cradle 200b is divided off from the power supplied to the cradle 200a, and is supplied via the electrode units 47 and 48. Normally, it is often the case that the remaining amounts of charge of the battery 13 of the cassettes 100 respectively charged in the cradle 200a and the cradle 200b are not the same. Accordingly, the electronic substrate 37 of the cradle 200a can charge efficiently by controlling the current amount to complete the charge first for the cassette 100 whose remaining amount of charge in the battery 13 is larger. Such control is realized by implementing a current control unit in the electronic substrate 37 of the cradle 200a.

Also, since the coupling portions 41A and 41B are provided in the housing unit 30 of the cradles 200a and 200b respectively, it is possible to prevent the coupling between the cradle 200a and the cradle 200b from easily unlocking.

Also, functions that cause the coupling portions 41A and 41B to connect mechanically are the engaging portions 42A, 42B, 43A, and 43B, and the connecting units 44A and 44B are configured separately for electrical connection. For this reason, it is possible to prevent a force acting on the connecting units 44A and 44B because even if an external force is loaded on the cradle 200a and the cradle 200b the engaging portions 42A, 42B, 43A, and 43B receive that force. Accordingly, it is possible to stably connect the electrode unit 47 and the electrode unit 48.

Note that in the present embodiment, explanation is given for a case in which two cradles 200 are installed, but limitation is not made to such a case, and three or more cradles 200 may be installed. For example, in the case of installing three cradles 200, coupling portions 41A similar to the coupling portions 41A of the side wall portion 32b of the cradle 200a are provided on the side wall portion 32b of the cradle 200b. Then, by coupling the coupling portions 41B of another cradle of the same structure as the cradle 200b to the coupling portions 41A it is possible to install three cradles 200 in a space economical manner.

Fifth Embodiment

In the fifth embodiment, explanation is given of a case in which by changing the shape of a portion of the cradle, installation space is further economized.

Figure 12A:
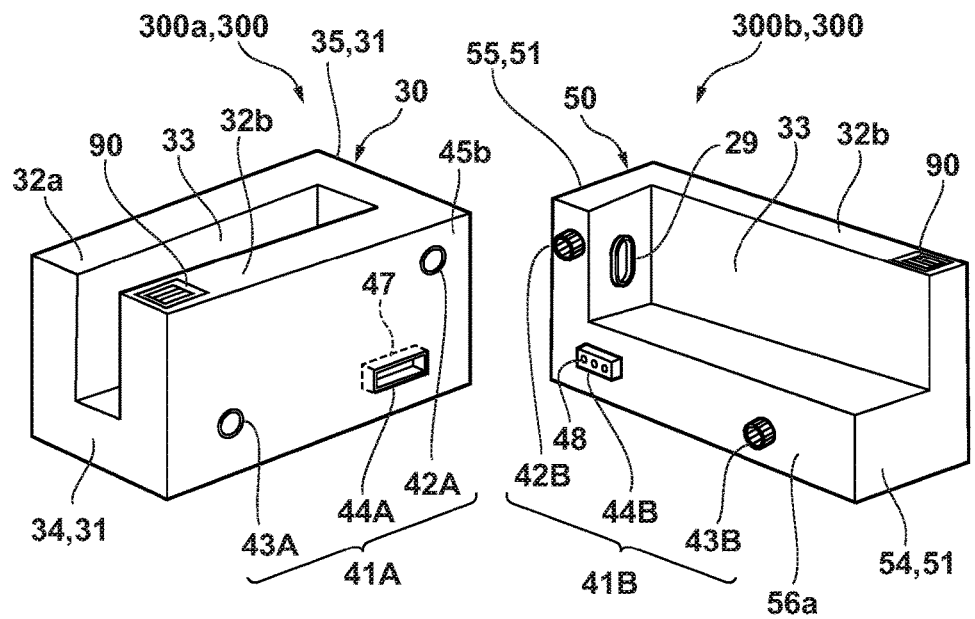
FIGS. 12A-12B are perspective views illustrating a cradle coupling structure according to a fifth embodiment.
Figure 12B:
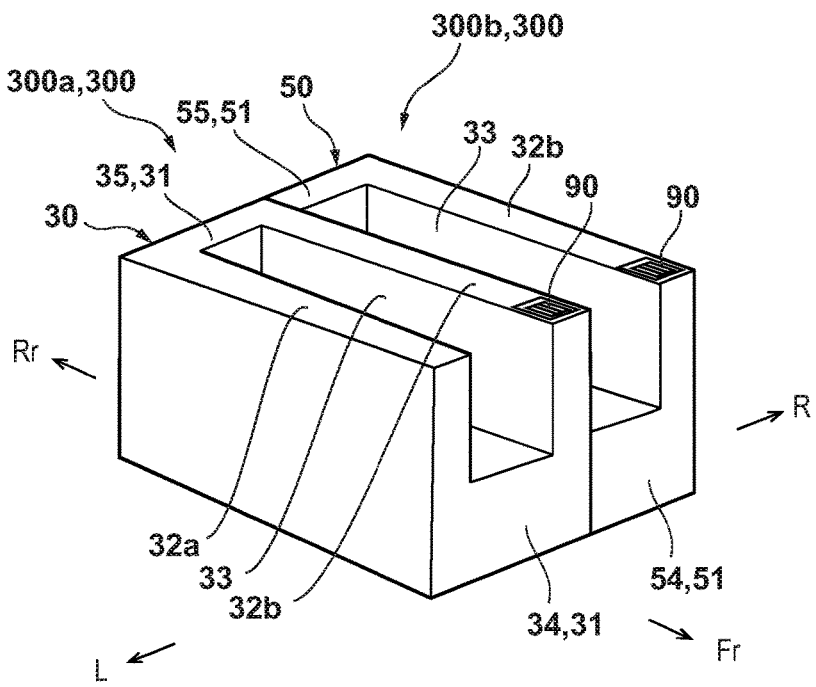

FIGS. 12A-12B are perspective views illustrating the coupling structures of a cradle 300. Specifically, FIG. 12A illustrates a state in which two of the cradle 300 are separated, and FIG. 12B illustrates an accommodation system in which two of the cradle 300 are coupled. Here, a cradle 300a is explained as the left side and an added cradle 300b as the right side. Below, explanation is focused on configuration different to the fourth embodiment, and the same reference numerals are given for the same configurations, and explanation thereof is omitted as appropriate.

The cradle 300a is substantially the same configuration as the cradle 200a of the fourth embodiment but the shape of the housing unit 30 is partially different. Specifically, for the cradle 300a, the housing unit 30 comprises a pair of side wall portions 32a and 32b, and the coupling portions 41A are provided on the side surface 45b of the side wall portion 32b.

Meanwhile, the cradle 300b is a configuration for which a housing unit 50 comprises a single side wall portion 32b. That is, the cradle 300b is of a shape that excludes the side wall portion 32a from the housing unit 30 of the cradle 300a. Also, for the cradle 300b, a space surrounded by a main body unit 51 which is made up of a bottom portion 54 and a support portion 55, and the single side wall portion 32b is the accommodation unit 33, and the opposite side of the side wall portion 32b is open.

In this way, for the cradle 300b, the left-right dimension of the housing unit 50 is smaller than the left-right dimension of the housing unit 30 of the cradle 300a by the amount that the side wall portion 32a is excluded.

Also, in the cradle 300b of the present embodiment, the coupling portions 41B coupled to the cradle 300a are provided on the side surface 56a of the main body unit 51. Specifically, the engaging portions 42B and 43B and the connector unit 44B are comprised on the side surface 56a of the main body unit 51.

Next, explanation is given of a case in which the cradles 300 are coupled to each other.

Firstly, the user causes the side wall portion 32b of the cradle 300a and the main body unit 51 of the cradle 300b to face each other. At this time, the engaging portion 42A and the engaging portion 42B, the engaging portion 43A and the engaging portion 43B, and the connector unit 44A and the connector unit 44B respectively face each other. Next, by the user pushing the cradle 300a and the cradle 300b in directions so that they approach each other, they are coupled in a state in which the side wall portion 32b of the cradle 300a and the main body unit 51 of the cradle 300b contact as illustrated in FIG. 12B.

Here, the accommodation unit 33 of the cradle 300b is surrounded by the side surface 45b of the side wall portion 32b of the cradle 300a. Accordingly, because the cassette 100 accommodated in the accommodation unit 33 of the cradle 300b is supported by the side surface 45b of the side wall portion 32b of the cradle 300a that is coupled, it is possible to stably support the cassette 100 even without the side wall portion 32a. Specifically, it is possible to use the side wall portion 32b of the cradle 300a as the side wall portion of the cradle 300b as well.

In this way, by coupling the cradle 300b which does not have the side wall portion 32a on the side of the side wall portion 32b of the cradle 300a, it is possible to miniaturize the cradle 300b by the amount in which the side wall portion 32a of the cradle 300b does not exist, and it is possible to achieve economization of installation space. Here it is possible for the cassette 100 accommodated in the accommodation unit 33 of the cradle 300b to be stably supported by the side wall portion 32b of the cradle 300a.

Note that in the present embodiment, explanation is given for a case in which two cradles 300 are installed, but limitation is not made to such a case, and three or more cradles 300 may be installed. For example, in the case of installing three cradles 300, coupling portions 41A similar to the coupling portions 41A of the side wall portion 32b of the cradle 300a are provided on the side wall portion 32b of the cradle 300b. Then, by coupling the coupling portions 41B of another cradle of the same structure as the cradle 300b to the coupling portions 41A it is possible to install three cradles 300 in a space economical manner.

Sixth Embodiment

In the sixth embodiment, explanation is given of a case in which the cradle is installed easily by making the side wall portion of the cradle detachable.

Figure 13A:
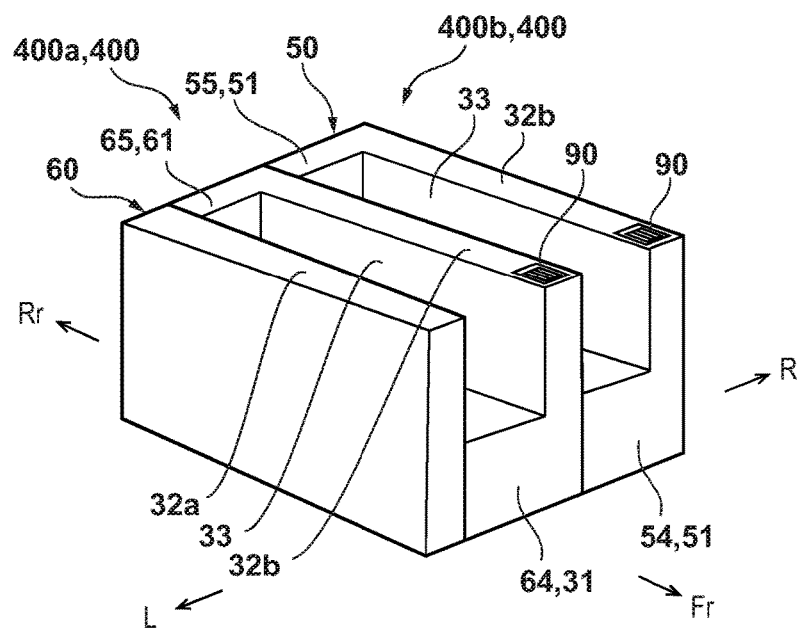
FIGS. 13A-13B are perspective views illustrating a cradle coupling structure according to a sixth embodiment.
Figure 13B:
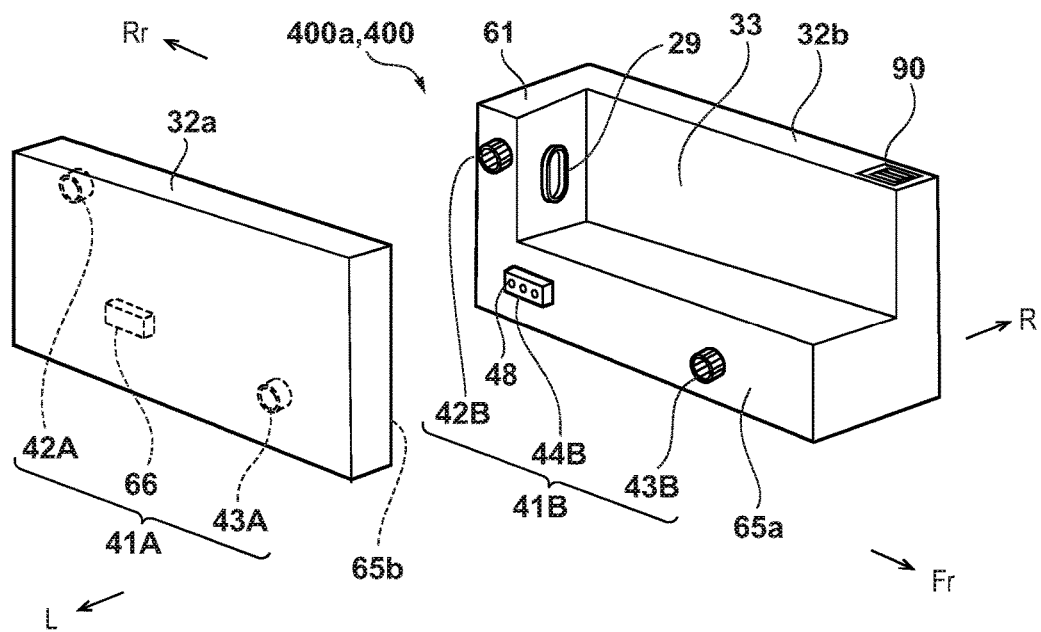

FIGS. 13A-13B are perspective views illustrating the coupling structures of a cradle 400. Specifically, FIG. 13A illustrates an accommodation system in which two of the cradle 400 are coupled, and FIG. 13B illustrates a configuration in which the side wall portion is detachable. Here, a cradle 400a is explained as the left side and a cradle 400b as the right side. Below, explanation is focused on configuration different to the fifth embodiment, and the same reference numerals are given for the same configurations, and explanation thereof is omitted as appropriate.

The cradle 400a is a structure from which the side wall portion 32a is detachable. Specifically, as illustrated in FIG. 13B, the side wall portion 32a is divided from a main body unit 61 of the cradle 400a. The side surface 65a of the main body unit 61 is the attachment/detachment surface for the side wall portion 32a.

Here, the coupling portions 41B that are coupled to the side wall portion 32a are provided on the side surface 65a of the main body unit 61. Specifically, the engaging portions 42B and 43B and the connector unit 44B are comprised on the side surface 65a of the main body unit 61 as the coupling portions 41B.

Meanwhile, in the side wall portion 32a the coupling portions 41A coupled to the coupling portions 41B are provided on the side surface 65b facing the main body unit 61. Specifically, the engaging portions 42A and 43A and a recessed portion 66 are comprised as the coupling portions 41A on the side surface 65b of the side wall portion 32a. The recessed portion 66 avoids interference with the connector unit 44B when the side wall portion 32a is coupled with the main body unit 61.

In this way, because it is possible to attach/detach the main body unit 61 and the side wall portion 32a via the coupling portions 41A and 41B, it is possible to separate the side wall portion 32a from the main body unit 61 of the cradle 400a. Accordingly, it is possible to couple via the coupling portions 41B another cradle that is of the same structure as the cradle 400a with the side surface 65a of the main body unit 61 from which the side wall portion 32a is separated, and it is possible to easily install a cradle.

Meanwhile, if it is desired that the cradles 400a and 400b be installed in separate places, the user pulls apart the cradle 400a and the cradle 400b. Then, by mounting the side wall portion 32a to the main body units 61 and 51 of the cradles 400a and 400b respectively, it is possible to install only one cradle corresponding to one cassette 100.

Also, because the cradle 400a comprises the display unit 90 on the side wall portion 32b which does not attach/detach from the main body unit 61, it is possible for the user to confirm the state of the battery 13 via the display unit 90 even if the side wall portion 32a is separated because the cradles 400 are coupled to each other. Note that the display unit 90 can be provided on at least one of the main body unit 61 and the side wall portion 32b.

Seventh Embodiment

In the seventh embodiment, explanation is given for a cradle comprising a coupling portion that is different to the fourth through the sixth embodiments.

Figure 14A:
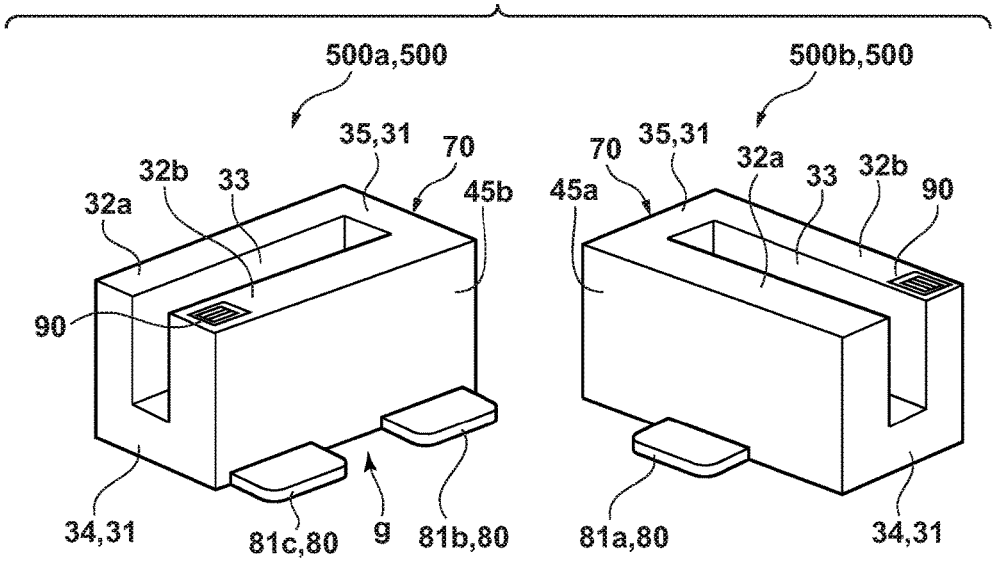
FIGS. 14A-14B are perspective views illustrating a cradle coupling structure according to a seventh embodiment.
Figure 14B:
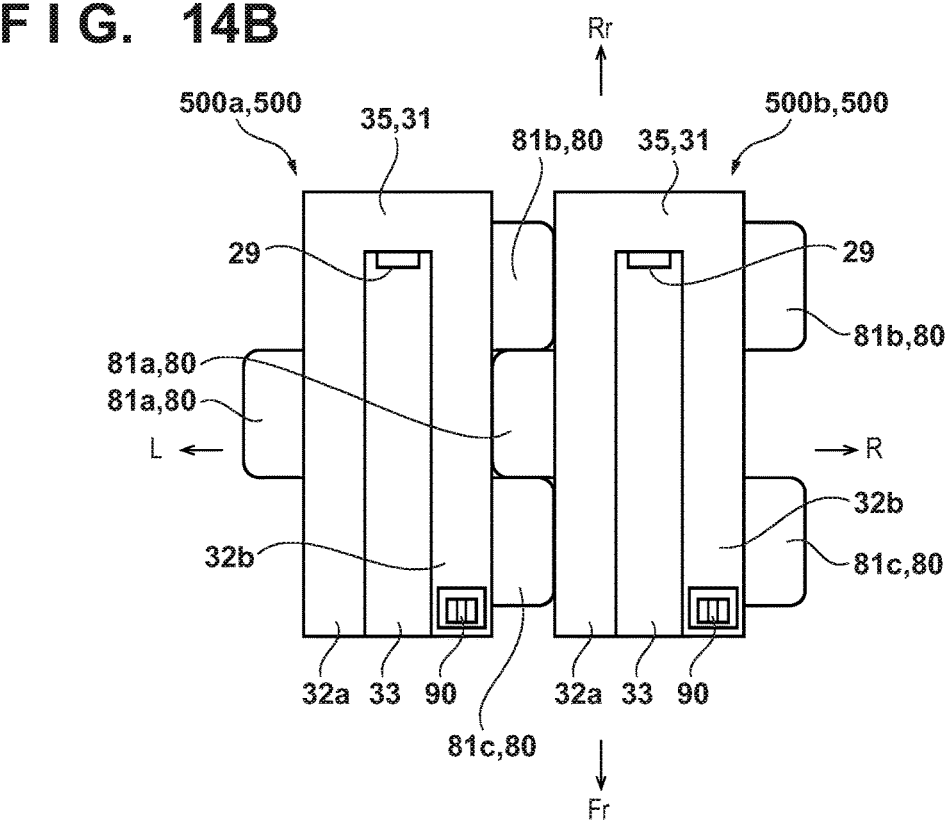

FIGS. 14A-14B are views illustrating the coupling structures of a cradle 500. Specifically, FIG. 14A illustrates a state in which two of the cradle 500 are separated, and FIG. 14B is a view of an accommodation system in which two of the cradle 500 are coupled seen from a top side. Here, a cradle 500a is explained as the left side and a cradle 500b as the right side. Below, explanation is focused on configuration different to the cradle 300a of the fifth embodiment, and the same reference numerals are given for the same configurations, and explanation thereof is omitted as appropriate. Note that the cradle 500a and the cradle 500b are of the same shape.

The cradle 500a comprises a leg 80 as a coupling portion of a housing unit 70. The leg 80 prevents the cradle 500a from falling after its center of gravity becomes too high when the cassette 100 is accommodated in the accommodation unit 33. Specifically, a first leg member 81a is formed integrally with the side wall portion 32a of the housing unit 70 (refer to the cradle 500b). The first leg member 81a is on a bottom side of the side wall portion 32a, and is positioned in the center of a front and back direction. Meanwhile, a second leg member 81b and a third leg member 81c are formed integrally in the side wall portion 32b. The second leg member 81b is on a bottom side of the side wall portion 32b, and is positioned on a rear side, and the third leg member 81c is on a bottom side of the side wall portion 32b, and is positioned on a front side. A gap g is formed between the second leg member 81b and the third leg member 81c.

Next, explanation is given of a case in which the cradles 500 are coupled to each other.

Firstly, the user causes the side wall portion 32b of the cradle 500a and the side wall portion 32a of the cradle 500b to face each other, and causes the cradle 500a and the cradle 500b to approach each other. Then, as illustrated in FIG. 14B, the first leg member 81a of the side wall portion 32a of the cradle 500b is inserted in the gap g between the third leg member 81c and the second leg member 81b of the side wall portion 32b of the cradle 500a. That is, in a state in which the first leg member 81a is positioned between the second leg member 81b and the third leg member 81c, the cradle 500a and the cradle 500b are coupled.

In this way, the first leg member 81a through the third leg member 81c cause the cradle 500a and the cradle 500b to be coupled, and they are arranged shifting the position in a direction (front and back direction) orthogonal to the direction (left-right direction) of coupling. Accordingly, because it is possible to cause the cradles 500a and 500b to approach each other without the first leg member 81a through the third leg member 81c being interfered with, it is possible to achieve economization of installation space even in a case where a plurality of cradles 500 are installed.

Note that in the present embodiment, explanation is given for a case in which two cradles 500 are installed, but limitation is not made to such a case, and three or more cradles 500 may be installed. Here, the same cradle as the foregoing cradles 500a and 500b can be used for the cradles that are installed.

Also, in the present embodiment, a single leg member 81a is formed on the side wall portion 32a, but two or more leg members may be formed. Also, in the present embodiment, explanation was given of a case in which two leg members 81b and 81c are formed in the side wall portion 32b, but a single leg member or three or more leg members may be formed. However, it is advantageous that the respective leg members be arranged to be shifted in the front and back direction when the cradles 500a and 500b are caused to approach each other in any case.

Also, in the present embodiment, explanation is given of a case in which the legs function to prevent the cradle 500 from falling, but limitation is not made to such a case. For example, the engaging portion 42B and the connector unit 44B described above may be provided on a proximal end of each leg member, and the engaging portion 42A and the connector unit 44A may be provided on the side wall portions 32a and 32b that face each other.

Eighth Embodiment

In the eighth embodiment, explanation is given for a case in which at least 2 accommodation unit shapes are different to each other among the accommodation units of the plurality of cradles.

Figure 15:
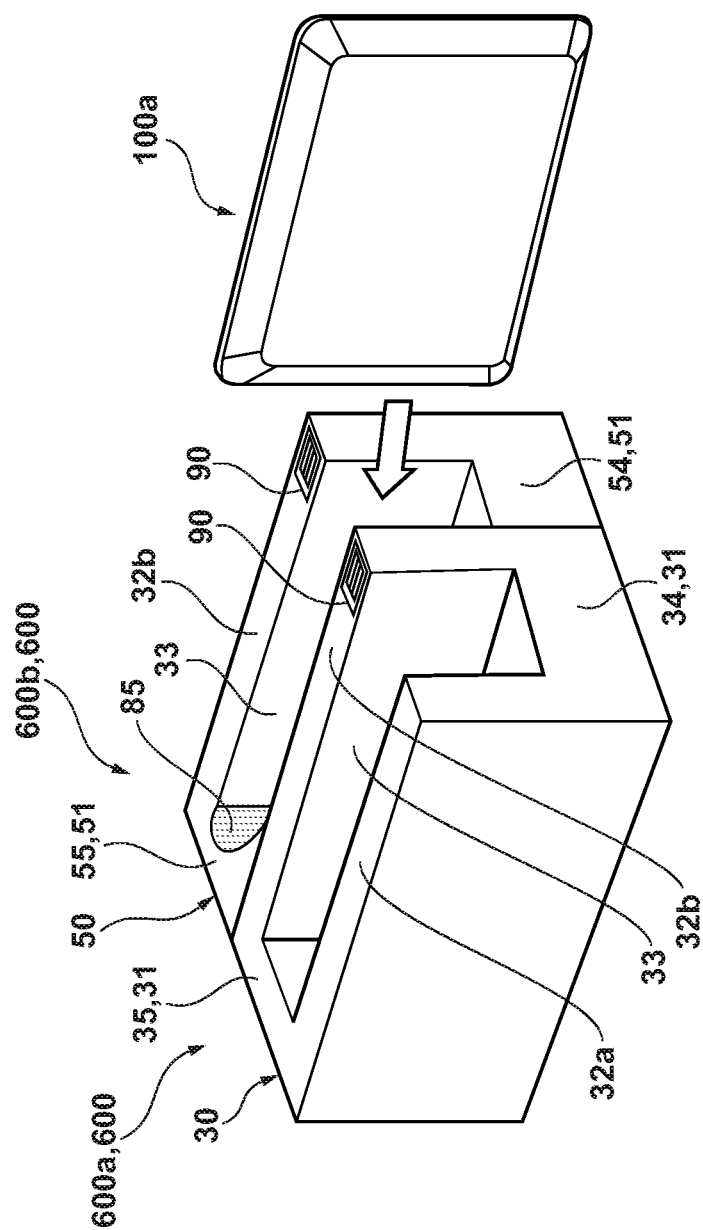
FIG. 15 is a perspective view illustrating a configuration of the cradle of an eighth embodiment.

FIG. 15 is a view illustrating a configuration of a cradle 600. Here, a cradle 600a is explained as the left side and a cradle 600b as the right side. Below, explanation is focused on configuration different to the fifth embodiment, and the same reference numerals are given for the same configurations, and explanation thereof is omitted as appropriate.

As illustrated in FIG. 15, for the housing unit 50 of the cradle 600b, the accommodation unit 33 is formed in a shape that matches the external form of the housing of the cassette 100a. Specifically, the accommodation unit 33 comprises a curved portion 85 formed in a curved form in the support portion 55 of the main body unit 51. That is, it is possible to accommodate only the cassette 100a which matches the shape of the accommodation unit 33 in the accommodation unit 33 of the cradle 600b. Accordingly, it is possible to limit the cassettes accommodated in the cradle 600b that accommodates the cassette 100a. Also, by causing the shape of the accommodation unit 33 to match the external form of the cassette 100a, it is possible to prevent the user from mistaking the direction in which to insert the cassette 100a.

Explanation has been given of the present invention together with various embodiments, but the present invention is not limited to these embodiments, and it is possible to make changes within the scope of the invention, and to combine the foregoing embodiments as appropriate.

Note that in the present embodiments described above, explanation is given of a case where the engaging portions 42A and 43A are assumed to be fitting holes and the engaging portions 42B and 43B are fitting bosses, but limitation is not made to such a case. The engaging portions 42A, 43A, 42B, and 43B may be structures that use magnetic force, a snap fit, a hook fitting or the like.

Also, in the above described embodiments, explanation is given of a case in which the power supply unit 39 is arranged on the deepest side of the support portion 35 of the housing unit 30, that is the accommodation unit 33, but limitation is not made to such a case, and it may be arranged on the side of the accommodation unit 33 of the side wall portions 32a and 32b or the bottom portion 34. However, by arranging the power supply unit 39 on the support portion 35, it is possible to easily design for a structure that can charge the cassette 100 whose size is different in one accommodation unit 33.

Also, in the above described embodiment, explanation is given for a case in which the power supply unit 39 is directly connected with the terminal 15 of the cassette 100, but limitation is not made to such a case, and the power supply unit 39 may be of a so-called non-contact power supply type. That is, the type and shape of a power receiving unit of the cassette 100 and the power supply unit 39 are not limited to a particular type and shape.

Also, in the above described embodiment, explanation is given for a case in which communication transmission/reception or power transmission/reception between a plurality of cradles is performed via the electrode units 47 and 48, but limitation is not made to such a case, and a non-contact power supply method such as electromagnetic induction, electric field resonance, or the like may be employed.

Also, in the above described embodiment, explanation is given of a case in which the cassette 100 comprises the battery 13 which can be attached/detached, but limitation is not made to such a case, and the cassette may comprise a built-in secondary battery.

Also, in the above described embodiment, explanation was given of a case in which the cradle charges in a state in which the battery 13 is mounted to the cassette 100, but limitation is not made to such a case. That is, the cradle may be a battery charger that charges the battery 13 after it is removed from the cassette 100. In such a case, it is possible to realize the shape of the accommodation unit 33 of the cradle by matching with the external form of the battery.

Also, in the above described embodiment, explanation is given of a case in which the display unit 90 is provided on the side wall portion 32b, but limitation is not made to such a case, and it may be provided on the main body unit 31.

Also, in the above described embodiment, explanation of a case in which the cradle comprises the power supply unit 39, and it is possible to charge the cassette 100, but limitation is not made to such a case, and it may simply be that the cassette 100 can be accommodated.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2015-210011, filed Oct. 26, 2015, and No. 2015-252018, filed Dec. 24, 2015, which are hereby incorporated by reference wherein in their entirety.

What is claimed is:

1. An accommodation apparatus that accommodates a radiation imaging apparatus in a cassette type, the accommodation apparatus comprising:
    an accommodation unit including a bottom surface, a first wall surface adjacent to the bottom surface, and a second wall surface adjacent to the bottom surface and provided at a position facing the first wall surface, wherein
    the length in a horizontal direction of the first wall surface adjacent to the bottom surface and the length in the horizontal direction of the second wall surface adjacent to the bottom surface are different so as to be capable of changing the direction of the radiation imaging apparatus as the radiation imaging apparatus is pulled out from the accommodation unit.

2. The accommodation apparatus according to claim 1, wherein
    the accommodation unit further comprises a third wall surface adjacent to the bottom surface, the first wall surface, and the second wall surface, and
    the third wall surface comprises a power supply unit configured to supply power to the radiation imaging apparatus when the radiation imaging apparatus is accommodated in the accommodation unit.

3. The accommodation apparatus according to claim 2, wherein the power supply unit is a power supply connector and supplies power in a state in which the radiation imaging apparatus is connected.

4. The accommodation apparatus according to claim 1, further comprising a display unit configured to display a charge status of the radiation imaging apparatus.

5. The accommodation apparatus according to claim 1, wherein a relation of L3>L1>L2 is satisfied, the length in the horizontal direction of the first wall surface being L1, the length in the horizontal direction of the second wall surface being L2, and the length in the horizontal direction of the bottom surface being L3.

6. The accommodation apparatus according to claim 1, wherein a relation of W>L1>L2 is satisfied, the length in the horizontal direction of the radiation imaging apparatus being W, in a case where the radiation imaging apparatus is accommodated, the length in the horizontal direction of the first wall surface being L1, and the length in the horizontal direction of the second wall surface being L2.

7. The accommodation apparatus according to claim 1, wherein relations L1>L2 and D1<D2 are satisfied, the length in the horizontal direction of the first wall surface being L1, the length in the horizontal direction of the second wall surface being L2, a thickness of a first wall surface portion including the first wall surface being D1, and a thickness of a second wall surface portion including the second wall surface being D2.

8. The accommodation apparatus according to claim 1, wherein the length in a vertical direction of the first wall surface and the second wall surface is configured to be shorter than the length of half the length in the vertical direction of the radiation imaging apparatus in a case where the radiation imaging apparatus is accommodated.

9. The accommodation apparatus according to claim 1, wherein the length in the horizontal direction of the second wall surface is configured to be shorter than the length of half the length in the horizontal direction of the radiation imaging apparatus in a case where the radiation imaging apparatus is accommodated.

10. The accommodation apparatus according to claim 1, wherein
the accommodation unit comprises a first housing unit, and a second housing unit configured to be capable of attachment/detachment in relation to the first housing unit, wherein
the length in the horizontal direction of the first wall surface and the length in the horizontal direction of the second wall surface are configured to be changed in accordance with attachment/detachment of the second housing unit in relation to the first housing unit.

11. The accommodation apparatus according to claim 1, further comprising a coupling portion configured to couple with another accommodation apparatus.

12. The accommodation apparatus according to claim 11, wherein the accommodation apparatus comprises a housing unit configured to accommodate the radiation imaging apparatus, and the coupling portion is provided in the housing unit.

13. The accommodation apparatus according to claim 12, wherein the housing unit includes:
a main body unit;
a side wall portion; and
the accommodation unit, the accommodation unit being surrounded by the main body unit and the side wall portion,
wherein an opposite side of the side wall portion is open, and
wherein the coupling portion is provided in a side surface on the opposite side of the side wall portion in the main body unit.

14. The accommodation apparatus according to claim 12, wherein the housing unit includes:
a main body unit;
a side wall portion configured to be detachable from the main body unit; and
the accommodation unit, the accommodation unit being surrounded by the main body unit and the side wall portion,
wherein the coupling portion is provided on an attachment/detachment surface to which the side wall portion is attached/detached in the main body unit.

15. The accommodation apparatus according to claim 14, wherein the coupling portion projects from the attachment/detachment surface.

16. The accommodation apparatus according to claim 11, wherein the coupling portion comprises an electrode unit configured to be electrically connected with the other accommodation apparatus, and to transmit/receive power with the other accommodation apparatus.

17. The accommodation apparatus according to claim 11, wherein the coupling portion comprises an engaging portion configured to be mechanically connected with the other accommodation apparatus.

18. The accommodation apparatus according to claim 14 wherein a side wall portion detachable from the main body unit is referred to as a first side wall portion,
wherein a coupling portion provided on the attachment/detachment surface is referred to as a first coupling portion,
wherein the housing unit includes:
a second side wall portion in a position facing the first side wall portion which sandwiches the accommodation unit; and
a second coupling portion for coupling with another accommodation apparatus on a side surface of the second side wall portion.

19. The accommodation apparatus according to claim 18, wherein a display unit is provided on at least one of the main body unit and the second side wall portion.

20. A radiation imaging system, comprising a radiation imaging apparatus including a radiation detector that converts radiation that is transmitted through an object into an electric signal, and a secondary battery that causes the radiation detector to operate; and
the accommodation apparatus according to claim 11.

* * * * *